US011712284B2

(12) United States Patent
Levin et al.

(10) Patent No.: US 11,712,284 B2
(45) Date of Patent: Aug. 1, 2023

(54) CONTROLLING BIPOLAR ABLATION IN MULTI-CHANNEL RF ABLATION DEVICES

(71) Applicant: Biosense Webster (Israel) Ltd., Yokneam (IL)

(72) Inventors: Michael Levin, Haifa (IL); Daniel Osadchy, Haifa (IL); Eyal Rotman, Kiriat Tivon (IL); Yavgeny Bonyak, Haifa (IL); Boris Ashkinezer, Akko (IL); Alek Vilensky, Netanya (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 495 days.

(21) Appl. No.: 16/673,851

(22) Filed: Nov. 4, 2019

(65) Prior Publication Data

US 2020/0205875 A1 Jul. 2, 2020

Related U.S. Application Data

(60) Provisional application No. 62/786,755, filed on Dec. 31, 2018.

(51) Int. Cl.
*A61B 18/12* (2006.01)
*A61B 18/00* (2006.01)
(Continued)

(52) U.S. Cl.
CPC .......... *A61B 18/1206* (2013.01); *A61B 18/16* (2013.01); *A61B 2018/0072* (2013.01);
(Continued)

(58) Field of Classification Search
None
See application file for complete search history.

(56) References Cited

U.S. PATENT DOCUMENTS

| 5,383,917 A | 1/1995 | Desai et al. |
| 8,456,182 B2 | 6/2013 | Bar-tal et al. |

(Continued)

FOREIGN PATENT DOCUMENTS

| EP | 1112720 A1 | 7/2001 |
| WO | WO 2019/159036 A1 | 8/2019 |

OTHER PUBLICATIONS

Extended European Search Report dated May 27, 2020, for Application No. 19220185.3, 8 pages.

*Primary Examiner* — Linda C Dvorak
*Assistant Examiner* — Nora W Rhodes
(74) *Attorney, Agent, or Firm* — Lewis Roca Rothgerber Christie LLP (57) ABSTRACT

An ablation system includes multiple electrodes configured to contact body tissue of a patient, including two or more ablation electrodes for contacting respective locations in a target organ and a return electrode. A signal-generating unit includes multiple signal generators, which are configured to apply respective composite signals to respective ones of the ablation electrodes. The composite signals include multiple, respective signal components, including respective ablation signals, having different, respective ablation-signal amplitudes and phases at a common ablation-signal frequency, and respective probe signals having respective probe-signal amplitudes and different respective probe-signal frequencies. A processor is coupled to measure the probe signals received by each of the multiple electrodes, and responsively to the measured probe signals, to control the ablation-signal amplitudes and phases.

20 Claims, 4 Drawing Sheets

(51) Int. Cl.
  *A61B 18/14* (2006.01)
  *A61B 18/16* (2006.01)
(52) U.S. Cl.
  CPC .............. *A61B 2018/0075* (2013.01); *A61B 2018/00351* (2013.01); *A61B 2018/00577* (2013.01); *A61B 2018/00702* (2013.01); *A61B 2018/00767* (2013.01); *A61B 2018/00791* (2013.01); *A61B 2018/00845* (2013.01); *A61B 2018/00875* (2013.01); *A61B 2018/126* (2013.01); *A61B 2018/1253* (2013.01); *A61B 2018/1467* (2013.01)

(56) References Cited

U.S. PATENT DOCUMENTS

| | | |
|---|---|---|
| 11,116,563 B2 | 9/2021 | Levin et al. |
| 2007/0255269 A1 | 11/2007 | Shin |
| 2008/0281322 A1* | 11/2008 | Sherman ............ A61B 18/1492 606/42 |
| 2009/0171345 A1 | 7/2009 | Miller |
| 2011/0163770 A1* | 7/2011 | Mahalingam ...... G01N 33/2823 324/693 |
| 2012/0116387 A1 | 5/2012 | Govari et al. |
| 2013/0035679 A1* | 2/2013 | Orszulak ............ A61B 18/1233 606/33 |
| 2015/0272655 A1 | 10/2015 | Condie et al. |
| 2017/0312025 A1* | 11/2017 | Harlev ................... A61B 18/14 |
| 2019/0201091 A1* | 7/2019 | Yates ................ A61B 18/1233 |
| 2019/0247108 A1* | 8/2019 | Levin ................ A61B 18/1492 |

* cited by examiner

CONTROLLING BIPOLAR ABLATION IN MULTI-CHANNEL RF ABLATION DEVICES

CROSS-REFERENCE TO RELATED APPLICATION

This application claims the benefit of U.S. Provisional Patent Application 62/786,755, filed Dec. 31, 2018, which prior application is hereby incorporated by reference as if set forth in full herein.

FIELD OF THE INVENTION

The present invention relates generally to therapeutic medical devices, and particularly to radiofrequency (RF) ablation devices and their manufacturing.

BACKGROUND

In a multi-channel ablation procedure, multiple ablation currents are applied, simultaneously, to multiple ablation electrodes.

U.S. Pat. No. 5,383,917 describes multi-phase RF ablation employing a two-dimensional or three-dimensional electrode array that produces a multitude of currents paths on the surface of the ablation zone. This results in a uniform lesion with a size defined by the span of the electrode array. An orthogonal electrode catheter array suitable for cardiac ablation is used in conjunction with a two-phase RF power source to produce uniform square-shaped lesions of size 1.2 $cm^2$. Lesions of larger size are created by successive adjacent placement of the square-shaped lesions. A temperature sensor at the electrode tip allows monitoring of ablation temperature and regulation of thereof to minimize the electrode tips from being fouled by coagulum.

United States Patent Application Publication 2008/0281322 describes a radio frequency tissue ablation system with a radio frequency generator. The generator comprises a radio frequency source, at least four independently controllable radio frequency outputs, a user interface and a controller configured to delivery radio frequency energy from the radio frequency source to the radio frequency outputs in one of at least two different output configurations in response to a configuration selection made through the user.

United States Patent Application Publication 2015/0272655 describes a system and method for preventing unintended tissue damage from the delivery of unintended bipolar radiofrequency energy. The system may include a multi-electrode ablation device and an RF delivery unit. The RF delivery unit may transmit unipolar energy to the plurality of electrodes, the energy being in phase, with all electrodes delivering the same voltage and being activated at the same time to deliver no bipolar energy. Additionally or alternatively, the RF delivery unit may transmit bipolar energy to the electrodes. Here, voltage differences between each pair of adjacent electrodes may be monitored and the level of bipolar energy being delivered may be calculated. The voltage of energy delivered to at least one electrode in each adjacent electrode pair may be adjusted if the amount of delivered bipolar energy exceeds a safety threshold.

SUMMARY

Embodiments of the present invention that are described hereinbelow provide improved RF ablation devices and methods for their operation.

There is therefore provided, in accordance with an embodiment of the invention, an ablation system, including multiple electrodes configured to contact body tissue of a patient, including two or more ablation electrodes for contacting respective locations in a target organ and a return electrode. A signal-generating unit includes multiple signal generators, which are configured to apply respective composite signals to respective ones of the ablation electrodes. The composite signals include multiple, respective signal components, including respective ablation signals, having different, respective ablation-signal amplitudes and phases at a common ablation-signal frequency, and respective probe signals having respective probe-signal amplitudes and different respective probe-signal frequencies. A processor is coupled to measure the probe signals received by each of the multiple electrodes, and responsively to the measured probe signals, to control the ablation-signal amplitudes and phases.

In the disclosed embodiments, each of the multiple signal generators includes an ablation-signal generator and a probe-signal generator. Each of the multiple signal generators includes a signal adder, coupled to the respective ablation-signal generator and the respective probe-signal generator, and the signal adder is configured to produce a respective composite signal by adding the respective probe signal to the respective ablation signal.

In some embodiments, the processor is configured to compute from the measured probe signals an admittance matrix between the multiple electrodes and to apply the admittance matrix in setting the ablation-signal amplitudes and phases.

Additionally or alternatively, the processor is configured to set the ablation-signal amplitudes and phases so as to cause respective unipolar and bipolar ablation currents to emanate from the electrodes into the body tissue. In some embodiments, the processor is configured to compute the respective amplitudes and phases of the ablation signals responsively to preset unipolar and bipolar ablation currents and the admittance matrix, wherein applying the computed ablation signals to the electrodes causes the preset unipolar and bipolar ablation currents to emanate from the electrodes. In a disclosed embodiment, the processor is configured to minimize a difference between the respective preset unipolar and bipolar ablation currents and the emanating unipolar and bipolar ablation currents. Additionally or alternatively, the processor may adjust the phases so as to control a ratio between the unipolar and bipolar ablation currents.

In a disclosed embodiment, the processor is configured to monitor changes in the probe signals during an ablation procedure, and to update the admittance matrix during the ablation procedure responsively to the changes.

In some embodiments, a ratio between the probe-signal amplitudes and the ablation-signal amplitudes is less than 1:15. Additionally or alternatively, the probe-signal frequencies differ from one another and from the ablation-signal frequency by at least 500 Hz.

In one embodiment, the multiple electrodes are disposed on a catheter, which is configured to contact a heart of the patient.

There is also provided, in accordance with an embodiment of the invention, a method for ablation, which includes placing multiple electrodes in contact with body tissue of a patient, including two or more ablation electrodes contacting respective locations in a target organ and a return electrode. Respective composite signals are applied to respective ones of the ablation electrodes, the composite signals including multiple, respective signal components, including respective ablation signals, having different, respective ablation-signal amplitudes and phases at a common ablation-signal frequency, and respective probe signals having different respective probe-signal frequencies. The probe signals received by each of the multiple electrodes are measured, and the ablation-signal amplitudes and phases are controlled responsively to the measured probe signals.

The present invention will be more fully understood from the following detailed description of the embodiments thereof, taken together with the drawings in which:

DETAILED DESCRIPTION OF EMBODIMENTS

Overview

RF ablation of tissue of a patient requires a minimum of two electrodes, typically an ablation electrode internal to the patient, and a return electrode which may be on the patient's skin. In this, simplest, configuration there is only one possible path for the ablating current. This type of energy transfer is termed unipolar energy transfer, and the ablating current is termed unipolar ablating current. A unipolar ablating current has its ablating effect concentrated in the tissue, between the ablation electrode and the return electrode.

In configurations with multiple internal ablation electrodes there are multiple possible paths for the ablating current—between pairs of ablation electrodes, as well as between any of the ablation electrodes and the return electrode. Energy transfer between internal electrodes is termed bipolar energy transfer, and the ablating current is termed bipolar ablating current. The ablating effect of a bipolar ablating current is typically concentrated in the superficial tissue between the internal electrodes. In general, for the case of multiple internal electrodes, there is the possibility of both unipolar and bipolar energy transfer, and the division of the ablating current between unipolar and bipolar currents may be used for controlling the spatial distribution of the ablation in the tissue.

In multi-electrode configurations, some of the ablating current may travel along unwanted paths. In general there may be intended and/or unintended unipolar ablating currents; there may also be intended and/or unintended bipolar ablating currents. For example, two internal electrodes may be energized so as to provide intended bipolar energy transfer, but their activation typically also provides unipolar energy transfer, which is unintended. As another example, the current from a given electrode may consist of intended unipolar ablating current, intended bipolar ablating current flowing to a certain internal electrode, and unintended bipolar ablating current flowing to another internal electrode.

Unipolar and bipolar ablation currents may be controlled by time-division multiplexing (TDM), wherein only one ablation electrode or a small subset of the electrodes are energized at a time. A drawback of TDM is that—besides being slow—the inherent switching from electrode to electrode generates parasitic frequencies, which may interfere with other devices (e.g., electro-cardiogram (ECG) devices) in the immediate environment.

Without sufficient metrology of both ablating currents and voltages, as well as without means to control the ablation currents, dividing the ablating current in a smoothly controlled fashion from any given electrode into intended unipolar and bipolar currents, with a minimal component of unwanted currents, is a challenging task.

Embodiments of the present invention that are described herein address these problems by incorporating into the network of electrodes and tissue identifiable probing signals, computing an admittance matrix for the network based on the probing signals, and computing the amplitudes and phases for the ablating voltages and currents of each electrode so as to achieve the required unipolar and bipolar ablating currents.

In the disclosed embodiments, the multiple ablation electrodes contacting the patient's tissue are energized by an electrode circuit similar to that used in United States Patent Application document Ser. No. 15/898,052, filed on Feb. 15, 2018, and published as US 2019/0247108, which prior application is herein incorporated by reference in its entirety into this application as though set forth in full, and which is further detailed below. The electrode circuit measures the current traversing each internal electrode in a multi-electrode system by driving a low-amplitude probe current through the electrode, either by itself or added to each high-amplitude ablation current. The probe current for each electrode has a different frequency unique to that electrode, which enables a measurement and identification of the probe current flowing through all electrodes, as well as the corresponding voltages on all electrodes. During an ablation procedure, each composite signal flows through a respective controlled gain stage, which is adjusted for feeding a pre-determined ablation signal power through the respective electrode.

The concept of using the phase of the ablation signals for controlling the relative amounts of unipolar and bipolar currents may be illustrated by a system with two internal electrodes (and a third return electrode): If the ablation voltages of the two internal electrodes have the same amplitude and frequency but are in antiphase, there is substantially no unipolar current, and 100% bipolar current. Alternatively, if the voltages of the two electrodes are in phase, then there is substantially no bipolar current, and 100% unipolar current. In general, the ratio between unipolar and bipolar ablation currents can be adjusted by adjusting the phase of the voltage at each electrode. The admittance matrix described above can be used in finding the appropriate adjustments.

As the electrical properties of the ablated tissue, as well as the contact resistances between the electrodes and the tissue, typically change during the ablation process, the probe currents and voltages are continuously monitored by a processor, which computes and updates the admittance matrix between all the electrodes.

System Description

Figure 1:
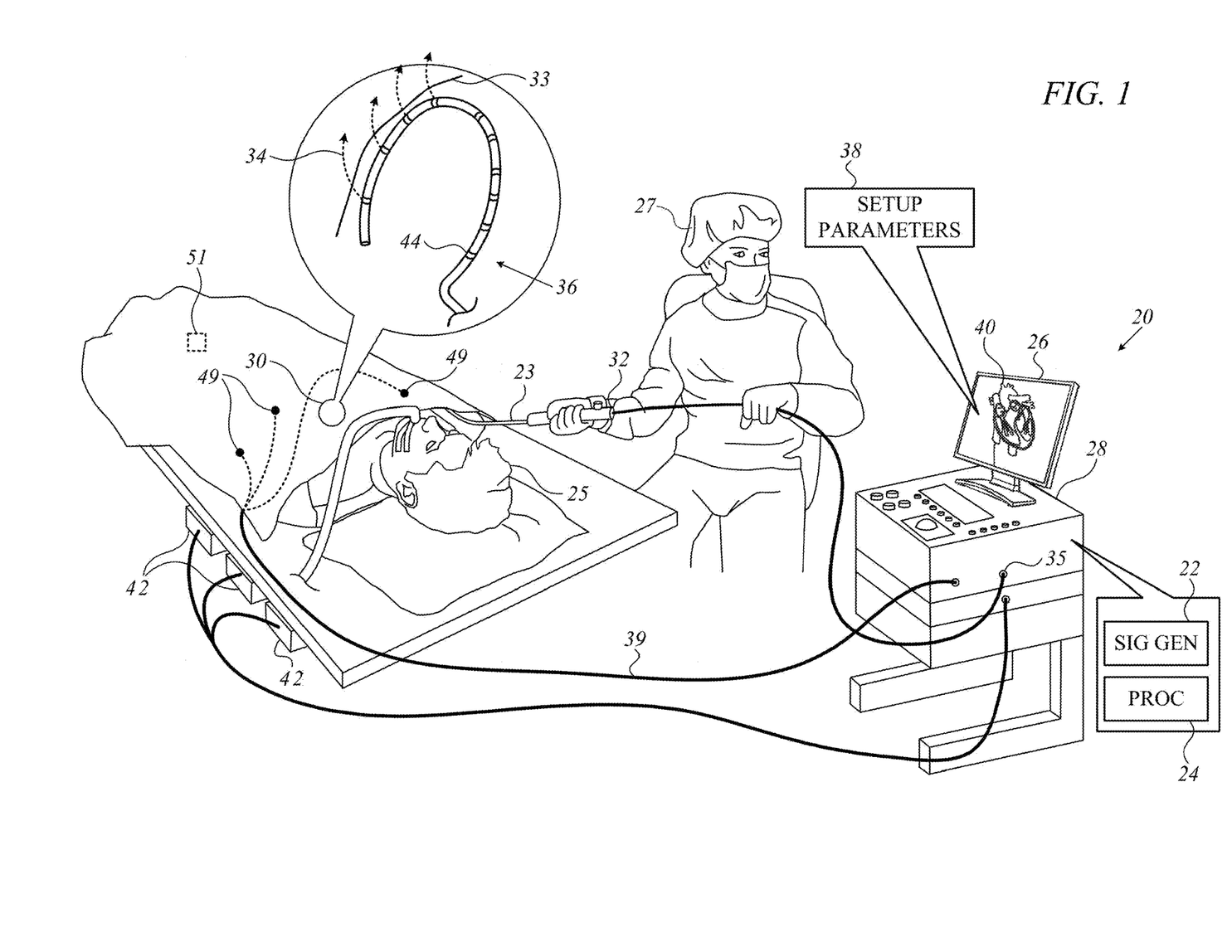
FIG. 1 is a schematic pictorial illustration of a multi-channel ablation system and procedure, in accordance with embodiments of the invention.

FIG. 1 is a schematic pictorial illustration of a multi-channel ablation system 20 and procedure, in accordance with embodiments of the invention. In the pictured embodiment, a physician 27 is performing a multi-channel cardiac ablation procedure using ablation system 20. Physician 27 is performing the procedure on a subject 25, using an ablation catheter 23 whose distal end 36 comprises multiple ablation electrodes 44.

To begin the procedure, physician 27 inserts catheter 23 into subject 25, and then navigates the catheter, using a control handle 32, to an appropriate site within, or external to, a heart 30 of subject 25. Subsequently, the physician brings distal end 36 into contact with tissue 33, such as myocardial or epicardial tissue, of heart 30. Next, a signal-generating unit (SIG GEN) 22 generates multiple signals 34, which are referred to herein as "composite signals" or "composite ablation signals," as explained below with reference to FIG. 3. Furthermore, a "signal" comprises both a current and a voltage; when necessary, a specific reference is made to either current or voltage. Signals 34 are carried through catheter 23, over different respective channels, to ablation electrodes 44, such that each electrode applies a different respective one of signals 34 to tissue 33 of subject 25.

In a unipolar ablation the currents of signals 34 flow between ablation electrodes 44 and an external electrode, or "return patch" 51, which is coupled externally between subject 25, typically on the skin of the subject's torso, to SIG GEN 22. In a bipolar ablation the currents of signals 34 flow between ablation electrodes 44.

Ablation system 20 further comprises a processor (PROC) 24. Processor 24 is configured to receive from physician 27 (or any other user), prior to and/or during the ablation procedure, setup parameters 38 for the procedure. For example, using one or more suitable input devices such as a keyboard, mouse, or touch screen, physician 27 selects one of two modes of ablation: (i) a current mode, or (ii) a power mode. In the current mode, physician 27 either sets the total ablation current for each electrode 44 or sets separately the desired levels for the unipolar current and the bipolar currents for the electrode. In the power mode, physician 27 either sets the total ablation power for each electrode 44 or sets separately the desired levels for unipolar power and the bipolar powers for the electrode, wherein the ablation power is computed from the voltage and current of the ablation signal, taking into account any phase shift between the two. While the description herein uses these two modes, it will be understood that the modes are example modes of ablation, and those having ordinary skill in the art will be able to adapt the description, mutatis mutandis, for other modes of ablation.

Physician 27 may also input, using the above mentioned input devices, for each ablation signal 34 (either for the total signal or separately for the unipolar and bipolar signals), a maximum power, a maximum current amplitude, a maximum voltage amplitude, a duration of the signal, and/or any other relevant parameters. (Typically, but not necessarily, these parameters are the same across all of the signals.) In response to receiving setup parameters 38, processor 24 communicates with signal-generating unit 22, so that the signal-generating unit generates signals 34 in accordance with the setup parameters. Additionally, the processor may display the setup parameters on a display 26 (which may comprise the aforementioned touch screen).

Processor 24 may be further configured to track the respective positions of ablation electrodes 44 during the procedure, using any suitable tracking technique. For example, distal end 36 may comprise one or more electromagnetic position sensors (not shown), which, in the presence of an external magnetic field generated by one or more magnetic-field generators 42, output signals that vary with the positions of the sensors. Based on these signals, the processor may ascertain the positions of the electrodes. Alternatively, for each electrode, processor 24 may ascertain the respective impedances between the electrode and multiple external electrodes 49 coupled to subject 25 at various different locations, and then compute the ratios between these impedances, these ratios being indicative of the electrode's location. As yet another alternative, the processor may use both electromagnetic tracking and impedance-based tracking, as described, for example, in U.S. Pat. No. 8,456,182, whose disclosure is incorporated herein by reference.

In some embodiments, the processor ascertains which of ablation electrodes 44 are in contact with the subject's tissue, and causes those electrodes, but not the other electrodes, to deliver signals 34 to the tissue. In other words, the processor may select a subset of channels leading to those electrodes that are in contact with the tissue, and then cause signals 34 to be passed over the selected subset of channels, but not over the other channels.

In some embodiments, the processor displays, on display 26, a relevant image 40 of the subject's anatomy, annotated, for example, to show the current position and orientation of distal end 36. Alternatively or additionally, based on signals received from relevant sensors disposed at distal end 36, the processor may track the temperature and/or impedance of tissue 33, and control signal-generating unit 22 responsively thereto. Alternatively or additionally, the processor may perform any other relevant function for controlling, or otherwise facilitating the performance of, the procedure.

Processor 24, and signal-generating unit 22, typically reside within a console 28, and both the processor and the signal-generating unit may each comprise one or several units. Catheter 23 is connected to console 28 via an electrical interface 35, such as a port or socket. Signals 34 are thus carried to distal end 36 via interface 35. Similarly, signals for tracking the position of distal end 36, and/or signals for tracking the temperature and/or impedance of the tissue, may be received by processor 24 via interface 35.

Processor 24 may typically comprise both analog and digital elements. Thus, processor 24 may comprise multiple analog-to-digital converters (ADCs) for receiving analog signals from signal-generating unit 22. Processor 24 may further comprise multiple digital-to-analog converters (DACs) for transmitting analog control signals to signal-generating unit 22. Alternatively, these control signals may be transmitted in digital form, provided that signal-generating unit 22 is configured to receive digital control signals. Processor 24 typically comprises digital filters for extracting signals at given frequencies from the received signals. Some or all of these components may be included in a field-programmable gate array (FPGA), such as a Cyclone Family FPGA by Intel of Santa Clara, Calif., USA.

Typically, the functionality of processor 24, as described herein, is implemented at least partly in software. For example, processor 24 may comprise a programmed digital computing device comprising at least a central processing unit (CPU) and random access memory (RAM). Program code, including software programs, and/or data are loaded into the RAM for execution and processing by the CPU. The program code and/or data may be downloaded to the processor in electronic form, over a network, for example. Alternatively or additionally, the program code and/or data may be provided and/or stored on non-transitory tangible media, such as magnetic, optical, or electronic memory.

Such program code and/or data, when provided to the processor, produce a machine or special-purpose computer, configured to perform the tasks described herein.

Notwithstanding the particular type of ablation procedure illustrated in FIG. 1, it is noted that the embodiments described herein may be applied to any suitable type of multi-channel ablation procedure.

The Equivalent Circuit and the Admittance Matrix

Figure 2:
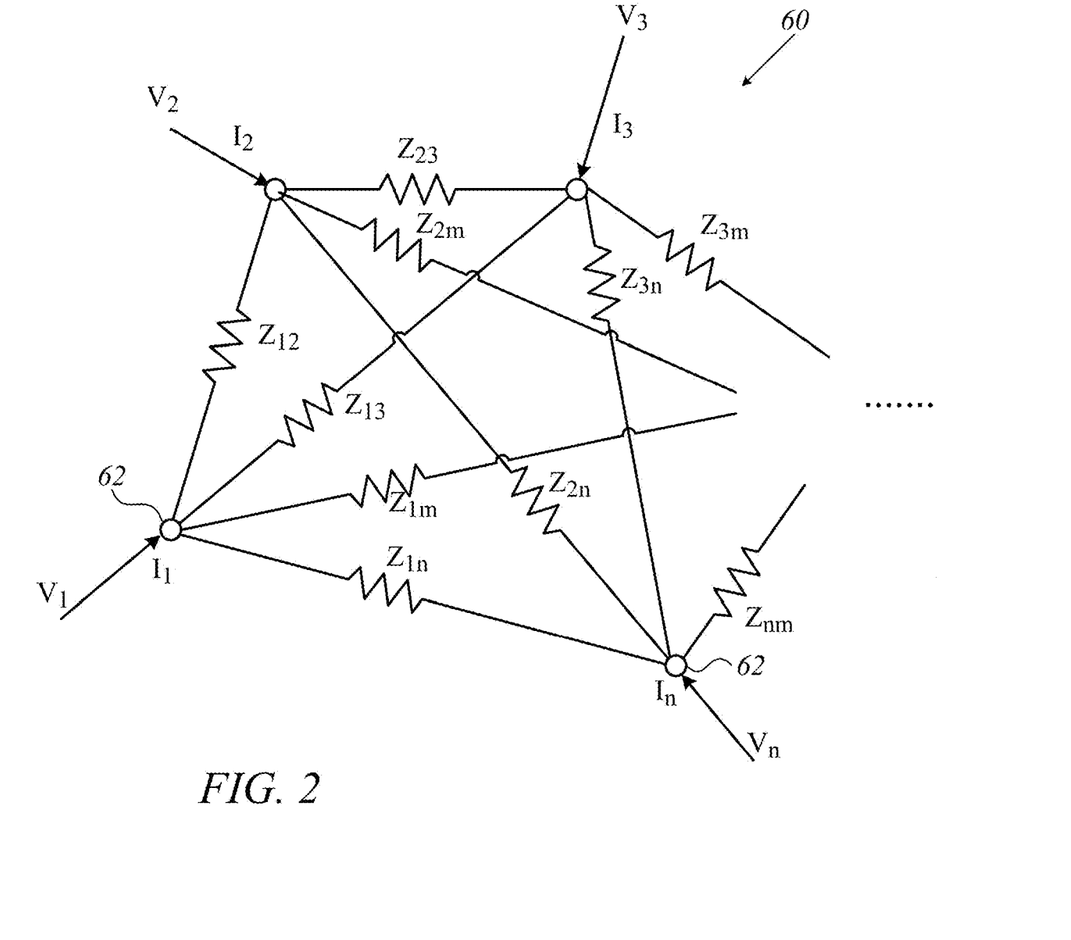
FIG. 2 is an electrical circuit diagram of an equivalent circuit that schematically represents an ablation circuit of n−1 ablation electrodes and an external electrode ("return patch"), in accordance with an embodiment of the invention.

FIG. 2 is a schematic illustration of an equivalent circuit 60 representing an ablation circuit of n−1 ablation electrodes and an external electrode ("return patch"), in accordance with an embodiment of the invention.

Equivalent circuit 60 comprises n nodes 62, numbered from 1 to n, representing n−1 ablation electrodes 44 and one external electrode 51. The index m refers to a general node 62. A current flowing through each node 62 sees an impedance to all the other nodes due to tissue 33 between the nodes, as well as to the contact resistance between the electrode and the tissue. In equivalent circuit 60 these impedances are represented as partial impedances $Z_{ij}$, wherein the indices i and j refer to nodes i and j. The impedances $Z_{ij}$ have complex values in general, leading to phase differences between the currents and voltages in equivalent circuit 60.

A current fed into node i of equivalent circuit 60 is labeled $I_i$, and the electrical potential (voltage) of the node is labeled $V_i$. Currents $I_i$ and voltages $V_i$ may be written in vector form as equations (1) and (2), respectively:

$$\vec{I} = \begin{bmatrix} I_1 \\ \vdots \\ I_n \end{bmatrix} \quad (1)$$

$$\vec{V} = \begin{bmatrix} V_1 \\ \vdots \\ V_n \end{bmatrix} \quad (2)$$

A linear relationship between the current and voltage vectors of equations (1) and (2) may be expressed by an n×n admittance matrix $\underline{Y}$ as equation (3):

$$\vec{I} = \underline{Y} \cdot \vec{V} \quad (3)$$

The elements $Y_{ij}$ of the admittance matrix $\underline{Y}$ may be written as equation (4):

$$Y_{ij} = \begin{cases} -1/Z_{ij} & i \neq j \\ \sum_{k \neq i} 1/Z_{ik} & i = j \end{cases} \quad (4)$$

The admittance matrix $\underline{Y}$ is symmetrical ($Y_{ji} = Y_{ij}$), and the sum of its rows is zero, reflecting the fact that the sum of all currents feeding into equivalent circuit 60 is zero. Due to the complex values of $Z_{ij}$, the admittance matrix $\underline{Y}$ is a complex-valued matrix.

One of nodes 62 (commonly taken as return patch 51) is generally chosen to be a "ground" or reference node r at zero potential, and the corresponding column in $\underline{Y}$ may be ignored (as it is multiplied by 0 in equation (3)). The corresponding row in $\underline{Y}$ may also be ignored, as the corresponding current may always be computed by summing the currents in all other nodes.

A modified current vector $\tilde{I}$ is defined as a vector comprising the currents of all nodes except reference node r, and a modified voltage vector $\tilde{V}$ is similarly defined as a vector comprising the voltages of all nodes except reference node r. Defining additionally a modified admittance matrix $\underline{\tilde{Y}}$ by removing from admittance matrix $\underline{Y}$ the rows and columns referring to reference node r, a linear relation between $\tilde{I}$ and $\tilde{V}$ may be written, similarly to equation (3), as equation (5):

$$\tilde{I} = \underline{\tilde{Y}} \cdot \tilde{V} \quad (5)$$

A comparison between the admittance matrices $\underline{Y}$ and $\underline{\tilde{Y}}$ is presented in Table 1, below.

TABLE 1

Comparison between admittance matrices Y and $\tilde{Y}$

| | Dimensions | Sum of rows |
|---|---|---|
| Y | n × n | 0 (singular matrix) |
| $\tilde{Y}$ | (n − 1) × (n − 1) | $\sum_{i=1}^{n-1} \frac{1}{Z_{ir}}$ |

In the calculations below, only admittance matrix $\underline{\tilde{Y}}$ will be used.

The Formalism for Extracting the Admittance Matrix $\tilde{Y}$

In order to measure the values of the elements of matrix $\underline{\tilde{Y}}$ for a given node k, an AC voltage source of frequency $f_k$ is connected between electrode k and reference electrode r, and the voltages and currents on all electrodes are measured, forming measurement vectors $\vec{V_k}$ and $\vec{I_k}$. The linear relation of equation (5) still holds, and may be written as equation (6):

$$\vec{I_k} = \underline{\tilde{Y}} \cdot \vec{V_k} \quad 6$$

Applying simultaneously n−1 external AC voltage sources with n−1 different frequencies $f_1, f_2, \ldots, f_{n-1}$ as probe signals to all n−1 electrodes, n−1 vectors $\vec{V_k}$ and $\vec{I_k}$ are measured, wherein the index k assumes the values from 1 to n−1 for the frequencies, and the n−1 elements in each vector refer to n−1 nodes 62. These vectors are assembled into respective (n−1)×(n−1) matrices $\underline{V}$ and $\underline{I}$. The relation between matrices $\underline{V}$ and $\underline{I}$ can now be written as equation (7):

$$\underline{I} = \underline{\tilde{Y}} \cdot \underline{V} \quad (7)$$

Equation (7) is valid for the n−1 frequencies $f_1, \ldots f_{n-1}$, i.e., matrix $\underline{\tilde{Y}}$ does not vary with these frequencies as long as they are limited to within a sufficiently narrow frequency band (to be detailed below). Admittance matrix $\underline{\tilde{Y}}$ can now be calculated through matrix inversion, given as equation (8):

$$\underline{\tilde{Y}} = \underline{I} \cdot \underline{V}^{-1} \quad (8)$$

Formalism for Calculating Bipolar and Unipolar Ablation Currents

For the calculations in the current section, an (n−1)×1 unit vector $\vec{1}$ is defined as a vector of length n−1, wherein every element of the vector is equal to 1. This vector is convenient for summing elements of vectors or matrices. (For example, $\vec{1}^T \cdot \vec{V}$ is the sum of elements of a vector $\vec{V}$, $\vec{1}^T \cdot \underline{S}$ is a sum of rows of matrix $\underline{S}$, $\vec{1}^T \cdot \underline{S} \cdot \vec{1}$ is a sum of all elements of matrix $\underline{S}$, and $\vec{1} \cdot V$ is a vector wherein every element is V.)

An ablation procedure is performed by applying ablation voltages, denoted by an ablation voltage vector $\vec{V}_{abl}$, between ablation electrodes 44 and external electrode 51. The elements of ablation voltage vector $\vec{V}_{abl}$ are the individual ablation voltages $V_i$ for each node i. The corresponding vector of all ablation currents can be calculated as equation (9):

$$\vec{I}_{abl} = \underline{\tilde{Y}} \cdot \vec{V}_{abl} \tag{9}$$

The ablation currents flow potentially into both unipolar and bipolar currents, except for the following two extreme cases:

1. Pure unipolar currents will flow when all electrode voltages are equal.
2. Pure bipolar currents will flow when the sum of all ablation currents (which is the total current flowing into external electrode 51) is zero.

Based on these two extreme cases, the ablation voltage vector $\vec{V}_{abl}$ can be separated to a sum of bipolar and unipolar parts, given as equation (10):

$$\vec{V}_{abl} = \vec{Vb} + \vec{1} \cdot Vu \tag{10}$$

where the bipolar voltage $\vec{Vb}$ is a vector and the unipolar voltage Vu is a scalar. The condition for pure bipolar currents above can be written as equation (11):

$$\vec{1}^T \cdot \underline{\tilde{Y}} \cdot (\vec{V}_{abl} - \vec{1} \cdot Vu) = 0 \tag{11}$$

Solving this for Vu yields equation (12):

$$Vu = \frac{\vec{1}^T \cdot \underline{\tilde{Y}} \cdot \vec{V}_{abl}}{\vec{1}^T \cdot \underline{\tilde{Y}} \cdot \vec{1}} \tag{12}$$

Now the unipolar current can be written as equation (13):

$$\vec{Iu} = \underline{\tilde{Y}} \cdot \vec{1} \cdot Vu = \underline{Y} \cdot \vec{1} \cdot \frac{\vec{1}^T \cdot \underline{\tilde{Y}} \cdot \vec{V}_{abl}}{\vec{1}^T \cdot \underline{\tilde{Y}} \cdot \vec{1}} = \frac{\underline{\tilde{Y}} \cdot \vec{1} \cdot \vec{1}^T \cdot \underline{\tilde{Y}}}{\vec{1}^T \cdot \underline{\tilde{Y}} \cdot \vec{1}} \cdot \vec{V}_{abl} \tag{13}$$

Based on equation (13), the unipolar and bipolar admittance matrices can be written as equations (14) and (15), respectively:

$$\underline{Y}^U = \frac{\underline{\tilde{Y}} \cdot \vec{1} \cdot \vec{1}^T \cdot \underline{\tilde{Y}}}{\vec{1}^T \cdot \underline{\tilde{Y}} \cdot \vec{1}} \tag{14}$$

$$\underline{Y}^B = \underline{\tilde{Y}} - \underline{Y}^U \tag{15}$$

where the element (i,j) of matrix $\underline{Y}^U$ is given by equation (16):

$$Y_{ij}^U = \frac{\left(\sum_k \tilde{Y}_{ik}\right)\left(\sum_k \tilde{Y}_{jk}\right)}{\sum_m \sum_k \tilde{Y}_{mk}} \tag{16}$$

The unipolar and bipolar currents are now given as equations (17) and (18), respectively:

$$\vec{Iu} = \underline{Y}^U \cdot \vec{V}_{abl} \tag{17}$$

$$\vec{Ib} = \underline{Y}^B \cdot \vec{V}_{abl} \tag{18}$$

The magnitudes of the unipolar and bipolar currents can now be controlled, based on equations (17) and (18), by the amplitudes and phases of the elements of ablation voltage vector $\vec{V}_{abl}$.

Optimization

Based on equations (17) and (18) for unipolar and bipolar currents, respectively, a cost function may be defined in order to calculate the ablation currents that will yield levels of unipolar and bipolar currents that are optimally close to the desired levels. In the optimization process, such values for the optimization targets are typically calculated that give a minimal value to the cost function and utilized in algorithm 120.

In an example, a target current vector for unipolar currents is written as $I_{target}^U$, and a target current vector for bipolar currents is written as $I_{target}^B$. A cost function cost($V_{abl}$) is defined by equation (19):

$$\text{cost}(V_{abl}) = a \sum_k \left((I_k^U \cdot I_k^{U*}) - I_{target}^{U\,2}\right)^2 + b \sum_k \left((I_k^B \cdot I_k^{B*}) - I_{target}^{B\,2}\right)^2 \tag{19}$$

In the above cost function, the parameters a and b are relative weights of the unipolar and bipolar currents, the asterisk (*) denotes a conjugate operation, and the optimization targets are the complex-valued elements of the ablation vector $\vec{V}_{abl}$. The target vectors as well as the relative weights are typically determined by physician 27.

Figure 3:
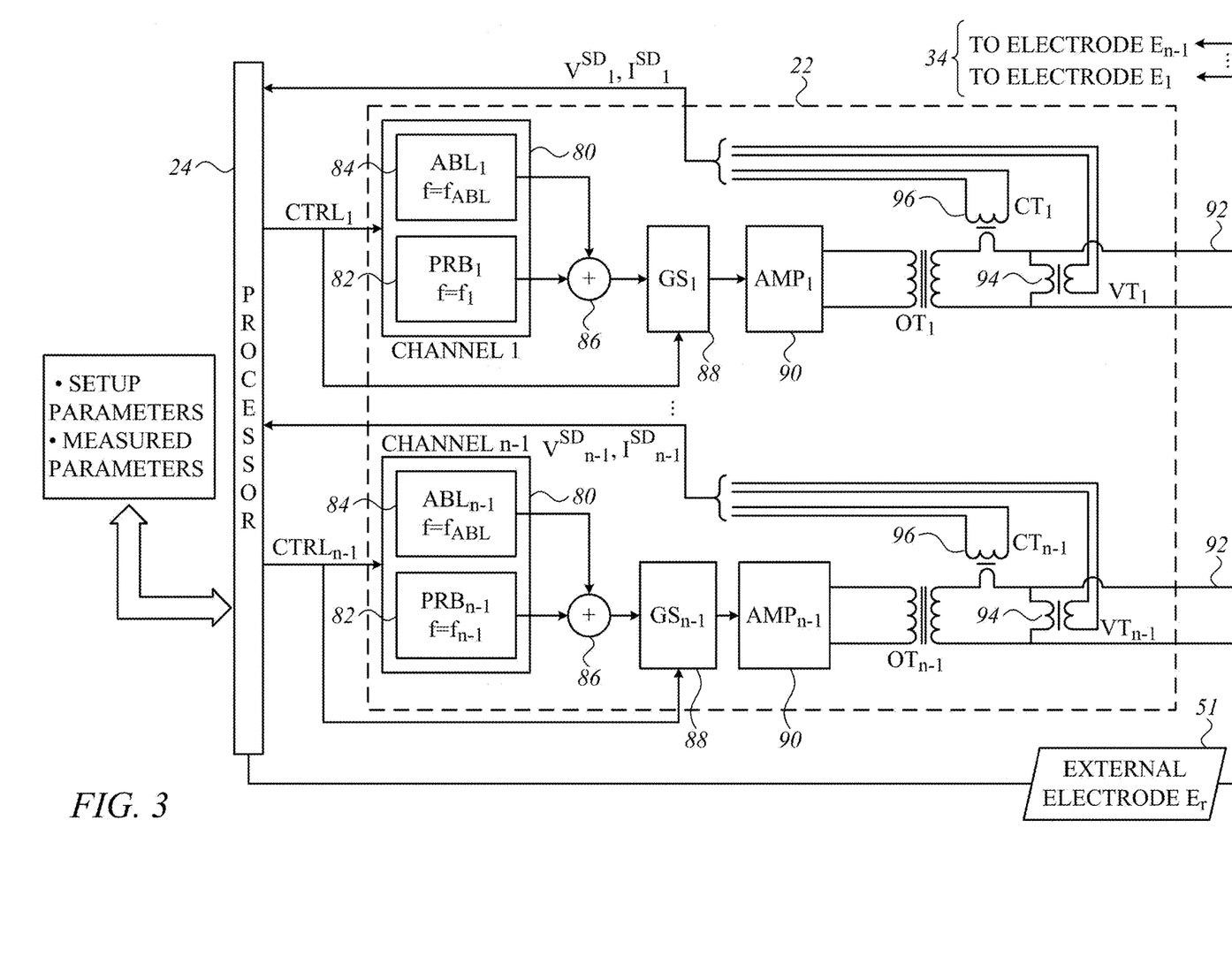
FIG. 3 is a schematic circuit diagram of a signal-generating unit, in accordance with embodiments of the invention.

FIG. 3 is a schematic circuit diagram of signal-generating unit 22, in accordance with embodiments of the invention. Signal-generating unit 22, in parts similar to the electrode circuit described in U.S. patent application Ser. No. 15/898,052, referenced above, comprises multiple signal generators 80, configured to generate signals 34, respectively, for application to subject 25 through ablation electrodes 44, as described above with reference to FIG. 1. In other words, each signal generator 80 is configured to generate a different, respective signal 34, to be passed through a corresponding electrode 44 to tissue 33 of subject 25.

FIG. 3 refers, following the previous treatment, to an ablation catheter 23 with n−1 ablation electrodes 44, with the ablation electrodes labeled $E_1, E_2, \ldots, E_{n-1}$, and external electrode (return patch) 51 labeled $E_r$.

Typically, each signal generator 80 comprises a probe-signal generator 82, configured to generate a probe signal at a unique probe-signal frequency $f_k$, an ablation-signal generator 84, configured to generate an ablation signal at an ablation signal frequency $f_{ABL}$, and a signal adder 86, configured to produce signal 34 (after gain control and amplification, as described below) by adding the generated probe signal to the generated ablation signal. By virtue of signal 34 being a combination of a probe signal and an ablation signal, it is referred to herein as a "composite signal" or "composite ablation signal," as noted above with reference to FIG. 1. The probe signals are utilized, independently from the ablation signals, for computing and updating the admittance matrix $\underline{\tilde{Y}}$.

All probe-signal generators 82 may emit their signals simultaneously, so that n−1 probe-signals at n−1 different frequencies may simultaneously be propagating within the circuit and sampled at each of the n−1 nodes.

While the probe signals have different respective probe-signal frequencies $f_k$, where k=1, . . . , n−1, the ablation signals typically have a single common ablation-signal frequency $f_{ABL}$. (The index "k" refers to the $k^{th}$ channel of the n−1 channels, as described below.)

In general, signal-generating unit 22 may comprise any suitable number of signal generators 80, corresponding to the number of ablation electrodes 44. For example, signal-generating unit 22 may comprise from two to twenty signal generators 80. FIG. 3 schematically illustrates n−1 signal generators 80 forming n−1 channels, by showing both the first and n−$1^{st}$ signal generator. The first ablation-signal generator 84 is indicated by the notation "ABL$_1$", while the n−$1^{st}$ ablation-signal generator 84 is indicated by the notation "ABL$_{n-1}$". Similarly, the first probe-signal generator 82 is indicated by the notation "PRB$_1$", while the n−$1^{st}$ probe-signal generator 82 is indicated by the notation "PRB$_{n-1}$".

In one embodiment, ablation-signal generators 84 are voltage sources, wherein the output voltage of each ablation-signal generator is set by an external control signal. In an alternative embodiment the ablation signal generators are current sources, wherein the output current is set by the external control signal.

Each ablation-signal generator 84 and probe-signal generator 82 may comprise a digital-to-analog converter, a stable analog free-running generator, or a direct digital synthesizer (DDS), such as the AD9854 DDS by Analog Devices, Inc., of Norwood, Mass., USA.

Typically, the smallest difference between any two of the probe-signal frequencies $f_k$ is large enough so as to inhibit the generation of problematic parasitic frequencies. For example, this difference may be greater than 500 Hz, which is the typical bandwidth of an ECG signal. Similarly, the difference between the ablation-signal frequency and the closest probe-signal frequency (i.e., the probe-signal frequency that is closest to the ablation-signal frequency, relative to the other probe-signal frequencies) is typically greater than 500 Hz. Nevertheless, the probe-signal frequencies are typically close enough to the ablation-signal frequency so that the probe signals and ablation signals have similar frequency-related effects on tissue 33.

For example, the difference between any pair of successive frequencies may be between 500 and 1500 Hz. In other words, (i) the difference between the ablation-signal frequency and the closest probe-signal frequency, and (ii) the difference between any pair of successive probe-signal frequencies that are both greater than or both less than the ablation-signal frequency, may be between 500 and 1500 Hz. (Two given frequencies are said to be "successive" if, when all of the frequencies are listed in order of increasing or decreasing magnitude, the two given frequencies are listed sequentially.) Thus, for example, given a difference of 1 kHz, an ablation-signal frequency $f_{ABL}$ of 486 kHz, and n−1 channels (assuming, for simplicity, that n−1 is even), the probe-signal frequencies $f_k$ may consist of 486−(n−1)/2 kHz, 486−(n−1)/2+1 kHz, . . . 485 kHz, 487 kHz, . . . 486+(n−1)/2−1 kHz, and 486+(n−1)/2 kHz.

Each probe-signal generator is configured to generate its probe signal such that the ratio between the amplitude of the probe signal and the amplitude of the ablation signal to which the probe signal is added is typically less than 1:15, such as less than 1:20, 1:40, 1:60, 1:80, 1:100, or 1:120, such that, by virtue of the relatively small amplitude of the probe signal, relatively little intermodulation distortion is introduced, and the contribution of the probe signals to the ablation power is negligible. For example, if, following the amplification of the composite signal as described below, the ablation signal has an amplitude of 90-110 V, the probe signal may have an amplitude of 1-2 V. Due to the frequency of the probe signal being similar to that of the ablation signal, the two signals see a similar admittance across the tissue of the subject, such that the ratio between the voltages of the two signals is generally the same as the ratio between the currents of the two signals.

Signal-generating unit 22 further comprises multiple controlled gain stages 88, configured to adjust the respective amplitudes of the composite signals during the application of the composite signals to the subject. Typically, signal-generating unit 22 comprises one controlled gain stage 88 for each signal generator 80, such that the output from each signal adder 86 is passed to a different respective controlled gain stage. FIG. 3 indicates the first controlled gain stage 88 by the notation "GS$_1$", and the n−$1^{st}$ controlled gain stage 88 by the notation "GS$_N$". Each controlled gain stage 88 may comprise, for example, a digital potentiometer, such as the AD5122 digital potentiometer by Analog Devices.

Typically, signal-generating unit 22 further comprises multiple amplifiers 90, configured to amplify the adjusted signals received from controlled gain stages 88. In FIG. 2, the first amplifier 90 is indicated by the notation "AMP$_1$", while the n−$1^{st}$ amplifier is indicated by the notation "AMP$_{n-1}$". The amplified signals 34 are output to ablation electrodes 44, over multiple channels 92. Typically, output transformers OT$_1$, . . . , OT$_{n-1}$ provide electrical isolation between the electrodes and signal generating unit 22.

Signal-generating unit 22 further comprises circuitry for each channel 92, such as a voltage transformer 94 and a current transformer 96, configured to step-down the voltage and current of signal 34 to measurable levels. For each channel i, the stepped-down voltage (e.g., the voltage induced across each voltage transformer 94, and indicated by notation $V^{SD}_i$) and the stepped-down current (e.g., the current induced through each current transformer 96, and indicated by notation $I^{SD}_i$) are input to the analog front-end of processor 24, and are then converted, by the analog-to-digital converter, to digital signals. These signals are then filtered, by the digital filter of processor 24, to extract the signal components at each of the different probe signal frequencies $f_k$. Subsequently, processor 24 calculates the voltage and current, $V_{PRB,ik}$ and $I_{PRB,ik}$, respectively, of the probe signals from the filtered signals for channel i and for each frequency $f_k$. There are a total of (n−1)×(n−1) probe signals for the n−1 frequencies from each one of the n−1 channels. For example, processor 24 may measure the amplitudes of the filtered signals, and then multiply each of these amplitudes by the appropriate transformer ratio to obtain $V_{PRB,ik}$ and $I_{PRB,ik}$.

From the measured values of $V_{PRB,ik}$ and $I_{PRB,ik}$ the elements of the admittance matrix $\underline{\tilde{Y}}$ are calculated by processor 24, as detailed above in the section entitled "FORMALISM FOR EXTRACTING THE ADMITTANCE MATRIX $\hat{\underline{Y}}$."

The ablation voltages $\vec{V}_{abl}$ for producing the desired levels of unipolar and bipolar currents are calculated by processor 24, as detailed above in the section entitled "OPTIMIZATION."

In current mode, processor 24 utilizes the admittance matrix $\hat{\underline{Y}}$ and the required ablation currents $I_i$ to compute updated values for the amplitudes and phases of the ablation voltages $V_i$. In power mode, these updated values are computed based on the required ablation powers.

During the procedure, processor 24 continually communicates n−1 sets of control parameters $CTRL_i$ to signal-generating unit 22. For example, these control parameters may include, for each channel i, the following: (i) an ON/OFF command for ablation-signal generator 84 ($ABL_i$), (ii) an ON/OFF command for probe-signal generator 82 ($PRB_i$), (iii) a signal to adjust the amplitude and phase of the output of ablation-signal generator 84 ($ABL_i$) (either voltage output or current output, depending on whether the ablation-signal generators are voltage sources or current sources), and (iv) a signal to adjust the gain of controlled gain stage 88 ($GS_i$). Control parameters $CTRL_i$ may be communicated directly from processor 24, or via any suitable hardware or other circuitry (not shown in FIG. 3).

Processor 24 may monitor additional parameters relevant for the ablation procedure. For example, processor 24 may continually (i) monitor the temperature at the interface between distal end 36 and tissue 33, (ii) responsively to this temperature, compute target ablation-signal powers, which do not exceed the maximum power specified by physician 27, and (iii) adjust the amplitudes and phases of the ablation voltages $V_i$ and currents $I_i$ and communicate the adjustments to signal-generating unit 22 via control parameters $CTRL_i$.

Alternatively or additionally to the circuitry described above (such as the signal generators, controlled gain stages, and amplifiers), signal-generating unit 22 may comprise any other suitable circuitry, such as, for example, output transformers for impedance matching, passive bandpass and/or band-stop filters, or passive overvoltage protection devices.

Figure 4:
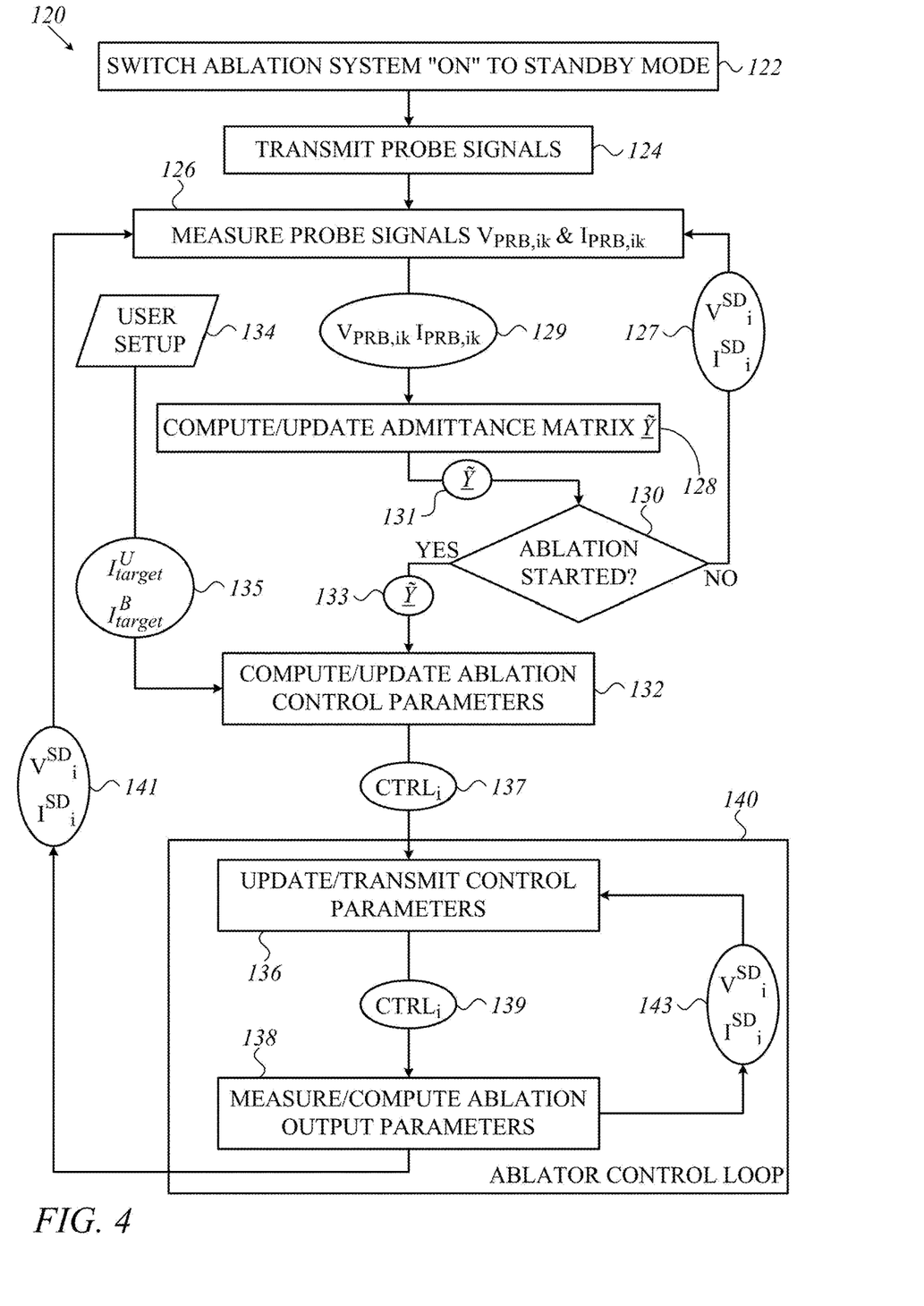
FIG. 4 is a flowchart that schematically illustrates feedback control loops for controlling ablation signals, in accordance with an embodiment of the invention.

FIG. 4 is an algorithm 120 (in the form of a flowchart) that schematically illustrates feedback control loops for controlling the ablation signals, in accordance with an embodiment of the invention. Algorithm 120 shows the major steps of the control loops. The main signals communicated between the steps are shown inside ovals.

In a standby step 122, ablation system 20 is turned on and goes into a standby mode. At this step, probe-signal generators 82 are turned on and can transmit probe signals, but no ablation signals are yet transmitted from ablation-signal generators 84. In a probe signal transmit step 124, probe signals at frequencies $f_k$ are transmitted from probe-signal generators 82 ($PRB_k$). In a probe signal measurement step 126, processor 24 measures and computes the probe signals $V_{PRB,ik}$ and $I_{PRB,ik}$ (as described above with reference to FIG. 3) by receiving the step-down signals $V^{SD}_i$ and $I^{SD}_i$, and by separating each frequency component of the probe signals through digital filtering.

Processor 24 further outputs the (n−1)×(n−1) probe signals (oval 129) to an admittance matrix computation step 128. At this step, processor 24 computes and updates the admittance matrix $\hat{\underline{Y}}$, and outputs it (oval 131) to a query step 130. In query step 130, processor 24 checks whether physician 27 has started the ablation process. If ablation has not started, processor 24 enters a loop comprising steps 126, 128, and 130, wherein the processor keeps measuring the probe signals from the received step-down signals (oval 127) and updating the admittance matrix $\hat{\underline{Y}}$. The fact that this loop runs in the absence of any ablation signals supports the use of the probe signals, independently of the ablation signals, for computing the admittance matrix $\hat{\underline{Y}}$.

Once the ablation starts, query step 130 transmits the admittance matrix $\hat{\underline{Y}}$ (oval 133) to a control parameter computation step 132. At this step, the desired levels of unipolar and/or bipolar currents $I_{target}^U$ and $I_{target}^B$ (oval 135) are received, for example as set by physician 27 in a user setup step 134. Processor 24 utilizes the desired levels of unipolar and bipolar currents and the admittance matrix to compute and update the control parameters $CTRL_i$. The updated control parameters (ovals 137 and 139) are transmitted to signal-generating unit 22 in a control parameter update/transmission step 136, and the amplitudes and phases of the ablation voltages $V_i$ are adjusted accordingly.

Processor 24 again receives the step-down signals $V^{SD}_i$ and $I^{SD}_i$ (ovals 141 and 143) and enters two feedback loops (i) and (ii):

(i) In a long feedback loop, the step-down signals $V^{SD}_i$ and $I^{SD}_i$ (oval 141) are again received into probe signal measurement step 126, leading to an update of the admittance matrix $\hat{\underline{Y}}$ in admittance matrix computation step 128, continuing through steps 130, 132, and 136. A continuous update of the admittance matrix $\hat{\underline{Y}}$ is useful, as both the properties of tissue 33 and the contact resistance between ablation electrodes 44 and tissue 33 may change during the ablation.

(ii) In a short ablator control loop 140, processor ascertains that none of the ablation parameters (voltages, currents, powers) exceed limits that may have been preset by physician 27 in user setup step 134, and updates the control parameters $CTRL_i$ as required, without taking into account possible changes in the admittance matrix $\hat{\underline{Y}}$. Control loop 140 is short in order to be able to respond in a timely fashion to potentially excessive ablation parameters. It is noted that algorithm 120 can be utilized by a skilled software engineer in this art to generate the requisite step-by-step computer codes for implementation of the overall method in a computer system (e.g., a general-purpose computer or a special purpose computer).

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:
1. An ablation system, comprising:
   (a) multiple electrodes configured to contact body tissue of a patient, including:
      (i) two or more ablation electrodes for contacting respective locations in a target anatomical structure, and
      (ii) a return electrode;
   (b) a signal-generating unit comprising multiple signal generators, which are configured to apply respective composite signals to respective ones of the ablation electrodes, the composite signals comprising multiple, respective signal components, including:

(i) respective ablation signals, having different, respective ablation-signal amplitudes and phases at a common ablation-signal frequency, and
(ii) respective probe signals having respective probe-signal amplitudes and different respective probe-signal frequencies; and
(c) a processor configured:
(i) to measure the probe signals received by each of the multiple electrodes,
(ii) to compute from the measured probe signals an admittance matrix between the multiple electrodes, and
(iii) to set the ablation-signal amplitudes and phases, responsively to the admittance matrix and desired levels of unipolar and bipolar currents, so as to cause respective selected unipolar and bipolar ablation currents to emanate from the electrodes into the body tissue.

2. The ablation system according to claim 1, each of the multiple signal generators comprising an ablation-signal generator and a probe-signal generator.

3. The ablation system according to claim 2, each of the multiple signal generators comprising a signal adder, coupled to the respective ablation-signal generator and the respective probe-signal generator, the signal adder being configured to produce a respective composite signal by adding the respective probe signal to the respective ablation signal.

4. The ablation system according to claim 1, the processor being configured to compute the respective amplitudes and phases of the ablation signals responsively to preset unipolar and bipolar ablation currents and the admittance matrix, such that applying the computed ablation signals to the electrodes causes the selected unipolar and bipolar ablation currents to emanate from the electrodes.

5. The ablation system according to claim 4, the processor being configured to minimize a difference between the respective preset unipolar and bipolar ablation currents and the emanating selected unipolar and bipolar ablation currents.

6. The ablation system according to claim 1, the processor being configured to adjust the phases so as to control a ratio between the selected unipolar and bipolar ablation currents.

7. The ablation system according to claim 1, the processor being configured to monitor changes in the probe signals during an ablation procedure, and to update the admittance matrix during the ablation procedure responsively to the changes.

8. The ablation system according to claim 1, a ratio between the probe-signal amplitudes and the ablation-signal amplitudes being less than 1:15.

9. The ablation system according to claim 1, the probe-signal frequencies differing from one another and from the ablation-signal frequency by at least 500 Hz.

10. The ablation system according to claim 1, the multiple electrodes being disposed on a catheter, which is configured to contact a heart of the patient.

11. A method for ablation, comprising:
(a) placing multiple electrodes in contact with body tissue of a patient, including two or more ablation electrodes contacting respective locations in a target anatomical structure and a return electrode;
(b) applying respective composite signals to respective ones of the ablation electrodes, the composite signals comprising multiple, respective signal components, including:
(i) respective ablation signals, having different, respective ablation-signal amplitudes and phases at a common ablation-signal frequency, and
(ii) respective probe signals having different respective probe-signal frequencies;
(c) measuring the probe signals received by each of the multiple electrodes; and
(d) responsively to the measured probe signals, controlling the ablation-signal amplitudes and phases,
a ratio between the probe-signal amplitudes and the ablation-signal amplitudes being less than 1:15.

12. The method according to claim 11, the act of applying respective composite signals comprising generating and summing the respective ablation signals and probe signals.

13. The method according to claim 11, the act of controlling the ablation-signal amplitudes and phases comprising computing from the measured probe signals an admittance matrix between the multiple electrodes and applying the admittance matrix in setting the ablation-signal amplitudes and phases.

14. The method according to claim 13, the act of applying the composite signals to the respective ablation electrodes comprising setting the ablation-signal amplitudes and phases, responsively to the admittance matrix, so as to cause respective selected unipolar and bipolar ablation currents to emanate from the electrodes into the body tissue.

15. The method according to claim 14, the act of controlling the ablation-signal amplitudes and phases comprising computing the respective amplitudes and phases of the ablation signals responsively to preset unipolar and bipolar ablation currents and the admittance matrix, the act of applying the computed ablation signals to the electrodes causing the selected unipolar and bipolar ablation currents to emanate from the electrodes.

16. The method according to claim 15, the act of computing the respective amplitudes and phases comprising minimizing a difference between the respective preset unipolar and bipolar ablation currents and the emanating selected unipolar and bipolar ablation currents.

17. The method according to claim 11, the probe-signal frequencies differing from one another and from the ablation-signal frequency by at least 500 Hz.

18. The ablation system according to claim 1, the processor being configured to compute the admittance matrix independently of the ablation signals.

19. A system, comprising:
(a) multiple electrodes configured to contact body tissue of a patient, including:
(i) two or more ablation electrodes for contacting respective locations in a target anatomical structure, and
(ii) a return electrode;
(b) a signal-generating unit comprising multiple signal generators, which are configured to apply respective composite signals to respective ones of the ablation electrodes, the composite signals comprising multiple, respective signal components, including:
(i) respective ablation signals, having different, respective ablation-signal amplitudes and phases at a common ablation-signal frequency, and
(ii) respective probe signals having respective probe-signal amplitudes and different respective probe-signal frequencies; and
(c) a processor configured:
(i) to measure the probe signals received by each of the multiple electrodes, (ii) to compute from the measured probe signals, independently of the ablation signals, an admittance matrix between the multiple electrodes, and (iii) to set the ablation-signal amplitudes and phases, responsively to the admittance matrix and desired levels of unipolar and bipolar currents, so as to cause respective selected unipolar and bipolar ablation currents to emanate from the electrodes into the body tissue.

20. The system according to claim 19, a ratio between the probe-signal amplitudes and the ablation-signal amplitudes being less than 1:15.

* * * * *